United States Patent
Ollerenshaw et al.

(10) Patent No.: US 6,866,686 B2
(45) Date of Patent: Mar. 15, 2005

(54) TISSUE GRAFT

(75) Inventors: Jeremy D. Ollerenshaw, Marietta, GA (US); Steven Goldstein, Atlanta, GA (US); Kirby S. Black, Acworth, GA (US)

(73) Assignee: Cryolife, Inc., Kennesaw, GA (US)

(*) Notice: Subject to any disclaimer, the term of this patent is extended or adjusted under 35 U.S.C. 154(b) by 117 days.

(21) Appl. No.: 09/769,769

(22) Filed: Jan. 26, 2001

(65) Prior Publication Data

US 2002/0128724 A1 Sep. 12, 2002

Related U.S. Application Data

(60) Provisional application No. 60/178,632, filed on Jan. 28, 2000.

(51) Int. Cl.⁷ .............................. A61F 2/36; A61F 2/04
(52) U.S. Cl. ...................................... 623/23.72; 600/36
(58) Field of Search ............................ 623/23.72–23.76, 623/15.11, 15.12, 1.44, 1.45, 1.46, 1.41, 1.47, 1.48

(56) References Cited

U.S. PATENT DOCUMENTS

| | | |
|---|---|---|
| 3,927,422 A | 12/1975 | Sawyer |
| 4,082,507 A | 4/1978 | Sawyer |
| 4,466,139 A | 8/1984 | Ketharanathan |
| 4,776,853 A | 10/1988 | Klement et al. |
| 4,801,299 A | 1/1989 | Brendel et al. |
| 4,902,508 A | 2/1990 | Badylak et al. |
| 5,192,312 A | 3/1993 | Orton |
| 5,336,616 A | 8/1994 | Livesey et al. |
| 5,595,571 A | 1/1997 | Jaffe et al. |
| 5,613,982 A | 3/1997 | Goldstein |
| 5,632,778 A | 5/1997 | Goldstein |
| 5,720,777 A | 2/1998 | Jaffe et al. |
| 5,762,600 A * | 6/1998 | Bruchman et al. ............ 600/36 |
| 5,762,966 A * | 6/1998 | Knapp et al. ................ 424/551 |
| 5,772,695 A | 6/1998 | Orton |
| 5,843,180 A | 12/1998 | Jaffe et al. |
| 5,843,181 A | 12/1998 | Jaffe et al. |
| 5,843,182 A | 12/1998 | Goldstein |
| 5,855,617 A | 1/1999 | Orton |
| 5,855,620 A | 1/1999 | Bishopric et al. |
| 5,863,296 A | 1/1999 | Orton |
| 5,899,936 A | 5/1999 | Goldstein |
| 5,993,844 A | 11/1999 | Abraham et al. |
| 6,010,529 A | 1/2000 | Herweck et al. |
| 6,039,755 A | 3/2000 | Edwin et al. |
| 6,048,360 A | 4/2000 | Khosravi et al. |
| 6,080,190 A | 6/2000 | Schwartz |
| 6,080,198 A | 6/2000 | Lentz et al. |
| 6,206,917 B1 | 3/2001 | Williams et al. |
| 6,371,992 B1 * | 4/2002 | Tanagho et al. ............ 424/423 |

FOREIGN PATENT DOCUMENTS

| | | |
|---|---|---|
| WO | WO 95/24873 | 9/1995 |
| WO | WO 96/32905 | 10/1996 |
| WO | WO 98/36707 | 8/1998 |
| WO | WO 98/49969 | 11/1998 |

OTHER PUBLICATIONS

Sutherland et al, "Regeneration of Bladder Urothelium, Smooth Muscle, Blood Vessels and Nerves Into an Acellular Tissue Matrix", The Journal of Urology 156(2S):571–577 (1996).

Wilson et al, "Acellular Matrix Allograft Small Caliber Vascular Prostheses", Trans. Am. Soc. Artif. Intern. Organs, vol. XXXVI, pp. M340–M343 (1990).

Wilson et al, "Acellular Matrix: A Biomaterials Approach for Coronary Artery Bypass and Heart Valve Replacement", Ann. Thorac. Surg. 60:S353–358 (1995).

Courtman et al, "The Acellular Matrix Vascular Prosthesis: Investigation of Its Potential as a Xenograft for Clinical Application", Advances in Biomateirals 10:241–246 (1992).

Uematsu and Okada, "Experimental studies on modified human ureter as an arterial substitution for reconstruction of small caliber vessels", Kobe J. Med. Sci. 42(5):291–306 (1996).

* cited by examiner

Primary Examiner—Corrine McDermott
Assistant Examiner—Hieu Phan
(74) Attorney, Agent, or Firm—Nixon & Vanderhye PC

(57) ABSTRACT

The present invention relates to a method of preparing a tissue graft material. The invention also relates to a multi-purpose tissue graft material and to methods of using same as a replacement for vascular and non-vascular tissue.

4 Claims, No Drawings

TISSUE GRAFT

The present application claims priority from Provisional Application No. 60/178,632, filed Jan. 28, 2000, the entire content of which is incorporated herein by reference.

TECHNICAL FIELD

The present invention relates to a method of preparing a tissue graft material. The invention also relates to a multi-purpose tissue graft material and to methods of using same as a replacement for vascular and non-vascular tissue.

BACKGROUND

In general, biological tissues have a better functional performance than equivalent synthetic devices when used as a body implant. Tissue grafts are presently largely limited to autologus and allograft tissues that have inherent supply constraints and logistic concerns of harvest, transportation and serologies. Accordingly, there is a need for additional sources of biological tissue grafts. Animal tissues represent such a source. Animal tissues can be relatively easily obtained from slaughterhouses in large quantities. Prior to use, however, these tissues must be treated to remove antigenic proteins that elicit a rejection response by the host following implantation.

Removal of antigenic proteins can be achieved by processing the donor tissue in a manner such that the cellular component of the donor tissue is removed. Many antigenic proteins are present on cellular membranes. Therefore, removal of cells also removes these proteins. After decellularization, the tissue can be packaged and sterilized for use as a biological graft. Grafts can be implanted into humans and other animals to repair, augment or replace natural structures, systems or existing prosthetic devices. These include but are not limited to, cardiovascular, vascular, urogenital, neurological, gastrointestinal and orthopedic systems. Grafts can also be used to provide hemodialysis access.

The present invention provides a method of processing animal tissue so as to render it suitable for implantation into a human (or non-human) host. The invention also provides a method for processing human tissue for use as an allograft implant.

SUMMARY OF THE INVENTION

The present invention relates to a method of preparing a tissue graft material and to the resulting multipurpose graft material. The invention also relates to a method of using the tissue graft as a replacement for vascular or non-vascular tissue.

Objects and advantages of the present invention will be clear from the description that follows.

DETAILED DESCRIPTION OF THE INVENTION

The present invention relates to a method of preparing an animal or human tissue in a manner so as to render it suitable for use in vascular and non-vascular graft applications. Tissue prepared in accordance with the method of the present invention exhibits physical and biological properties that render it particularly well adapted for tissue graft applications.

Tissue suitable for use in the present invention can be obtained from human cadavers or from bovine, porcine or other animal, for example, under abattoir conditions. Tissue can be transported to the point of tissue preparation under conditions necessary to keep the tissue at a desired temperature. Tissues can be transported, for example, immersed in a physiological salt solution and, upon arrival, inspected, washed, for example, in a physiological salt solution, and cleaned (dissected) free of unwanted adherent material, such as connective tissue and fat.

In a preferred embodiment, an isolated ureter is the tissue graft material. However, other tissues can be used including arteries, veins, tendons, heart valves, fascia lata, pericardium and nerves.

After collection and dissection, the transplant tissue is advantageously, first washed, for example, with phosphate buffered saline (PBS), to reduce microbial bioburden. The tissue is then incubated (e.g., at about 37° C. for about 18 hours) in a solution containing one or more antimicrobial agents, for example, an antibiotic or an antifungal agent, or mixture thereof, to further reduce the bioburden. Preferred antibiotics include amakacin, lincomycin, cefotaxime, vancomycin, rifampin, diflucan and amphotericin B. Advantageously, a mixture of these antibiotics is used. The tissue can then be cryopreserved for further processing at a later time or immediately subjected to decellularization.

Decellularization is preferably accomplished by incubating the tissue in a solution effective to lyse native cells in the tissue. Advantageously, the tissue is incubated (e.g., at about 37° C.) in sterile water (for example, for about 4 hours in the case of ureters), however an aqueous hypotonic buffer or low ionic strength buffer can also be used. If desired, the decellularizing solution can include other agents, such as protease inhibitors ((e.g., chelators such as EDTA)).

After decellularization, the resulting tissue matrix is treated with an enzyme (e.g., nuclease) cocktail to degrade nuclear material. Nucleases that can be used for digestion of native cell DNA and RNA include both exonucleases and endonucleases. Other nucleases are suitable for use in this step of the process and are commercially available. For example, a cocktail can be used comprising DNAse I (SIGMA Chemical Company, St. Louis, Mo.) and RNAse A (SIGMA Chemical Company, St. Louis, Mo.).

Preferably, the nucleases are present in a buffer solution that contains magnesium and calcium salts (e.g., chloride salts). The ionic concentration and pH of the buffered solution, the treatment temperature and the length of treatment are selected to assure the desired level of effective nuclease activity. In the case of ureters, the buffer is preferably a Tris buffer at pH 7.6. Preferably, the nuclease cocktail contains about 0.1 $\mu$g/ml to 50 $\mu$g/ml, preferably 17 $\mu$g/ml, of DNAse I, and about 0.1 $\mu$g/ml to 50 $\mu$g/ml, preferably 17 $\mu$g/ml, of RNAse A. The nuclease treatment can be effected at, for example, about 20° C. to about 38° C., preferably at about 37° C., for about 1 to 36 hours. In the case of ureters, nuclease treatment for about 19 hours is typically sufficient.

Subsequent to decellularization and nuclease treatment, the resultant tissue matrix can be treated (washed) to assure removal of cell debris which may include cellular protein, cellular lipids, and cellular nucleic acid, as well as extracellular debris, such as extracellular soluble proteins, lipids and proteoglycans. Removal of cellular and extracellular debris reduces the likelihood of the transplant tissue matrix eliciting an adverse immune response from the recipient upon implant. For example, the tissue can be incubated in a buffer (e.g., PBS) or in a detergent solution such as a solution of Triton X-100 in water. The composition of the solution, and the conditions under which it is applied to the tissue matrix can be selected to diminish or eliminate the activity of the nuclease utilized during nuclease processing and to remove cell debris. The process can include incubation at a temperature of between about 2° C. and 42° C., with 37° C. being preferred. The tissue matrix can be incubated in the detergent solution for up to 7 days, about 24 hours being sufficient in the case of a ureter matrix. When buffer is used rather than a detergent solution, the tissue matrix can be incubated for up to 30 days, about 14 days being sufficient in the case of a ureter matrix.

If used, the detergent solution can be washed out of the tissue matrix using multiple washes in a sterile aqueous solution (e.g., water). Optimum wash number and times can be readily determined, however, about 4 30 minute washes are preferred in the case of ureter matrices.

After washing, the tissue matrix can then be packaged, sterilized and/or stored prior to implantation. Advantageously, packaged tissue matrix is maintained in a non-frozen state, preferably at a temperature between 0° C. and 40° C., more preferably, between 0° C. and 20° C., most preferably between 2° C. and 8° C. up to and during sterilization using, for example, the approach used in Example 11. After sterilization, the tissue matrix can be maintained at room temperature. If desirable, the tissue matrix can be cryopreserved before or after sterilization for later use. Techniques of cryopreservation of tissue are well known in the art. Brockbank, K. G. M. Basic Principles of Viable TissuePreservation. In: Transplantation Techniques and use of Cryopreserverd Allograft Cardiac Valves and Vasular Tissue. D. R. Clarke (ed.), Adams Publishing Group, Ltd., Boston. pp 9–23, discusses cryopreservation of tissues and organs and is hereby incorporated by reference.

Tissue matrices of the invention, whether or not previously cryopreserved, can be sterilized using art recognized sterilization techniques. Advantageously, sterilization is effected using gamma irradiation at a dose of between 10 kGy and 100 kGy, preferably between 20 kGy and 40 kGy, more preferably between 25 kGy and 40 kGy. Alternative modes of sterilization include iodine peracetic acid treatment or electron beam. After sterilization, the tissue matrix can be stored frozen or unfrozen prior to implantation. If stored cryopreserved, for example, in liquid nitrogen, the tissue matrix is stable for at least 5 years. Prior to using a frozen tissue matrix, the matrix is thawed using a protocol designed to elute cryoprotectant solutions. For example, the matrix can be thawed rapidly to 4° C. in a waterbath at a temperature of 37–42° C. The matrix can then be quickly transferred to a growth medium such as Dulbeccos' Modified Eagles Medium (DMEM) containing mannitol (e.g., at about 0.5%). Mannitol and residual cryoprotectants can be removed by serial dilution (washing) with 0.5, 0.25 and 0.0M solutions of mannitol in DMEM. Following the washes, the tissue is ready to be used. For tissues not stored frozen, alternate washing protocols can be used, for example, washing in PBS or DMEM. Art-recognized implantation procedures can be used and the procedure selected is dependent on the tissue matrix used and site of implantation.

The tissue matrix resulting from the above-described process, particularly a ureter matrix, can be used as a conduit (tubular) graft. For example, a ureter matrix can be used as a vascular graft, nerve guide, or replacement for any tubular structure, including a ureter. When used as a conduit graft, the diameter of the graft should generally be about the same as the diameter of the native structure. The grafts of the invention demonstrate favorable characteristics as hemodialysis access grafts.

For use in other graft applications, a conduit graft (e.g., ureter tissue matrix) resulting from the above process can be cut longitudinally and rolled out to form a patch of tissue. The entire decellularization/nuclease treatment procedure described above can be carried out on patches of tissue (e.g., ureter tissue) prepared by cutting the segment longitudinally and unrolling it to form a pre-graft patch. The prepared graft patches can be utilized, for example, as a skin graft material or for repair of other body tissue defects lending themselves to surgical application of a tissue graft patch having the physical and functional characteristics of the present graft composition.

The tissue matrix of the present invention acts as a scaffold for spontaneous repopulation by host cells in vivo leading to tissue reconstruction and stabilization. The result is a fully functional, non-immunogenic, viable construct containing autologous cells expressing contractile proteins. The better patency rate and lack of infection seen in the present grafts may be attributable to the early incorporation, recellularization and remodeling of the matrix with host cells.

Certain aspects of the present invention are described in greater detail in the non-limiting Examples that follow.

EXAMPLE 1

Implantation of Decellularized Bovine Ureter as a Peripheral Vascular Graft in the Dog Methods Fresh bovine ureters were collected from slaughterhouses within 2 hours of death and shipped to the processing facility at 4° C. in a solution of phosphate buffered saline (PBS) to prevent tissue degradation in transit. Upon receipt of the tissue, a gross tissue inspection was made and ureters of 4 mm outside diameter and 30 to 40 cm in length were selected for processing. Selected ureters were dissected using sterile instruments to remove unwanted adherent material such as connective tissue and fat. Ureters were then placed in 300 ml capcity polypropylene containers and washed four times with 250 ml sterile PBS to reduce microbial bioburden. Ureters were then taken through steps to remove the tissue cell and antigen content.

Decellularization was initiated by incubation in a cocktail of antibiotics and antimycotic agents which consisted of a solution of antibiotics. This mixture contained the following: amakacin (34 µg/ml), lincomycin (160 µg/ml), cefotaxime (181 µg/ml), vancomycin (136 µg/ml), rifampin (82 µg/ml), diflucan (120 µg/ml) and amphotericin B (0.5 µg/ml). Incubation was for 18 hours in a shaking incubator at 37° C. For cell lysis, the antibiotic solution was replaced with 250 ml of sterile water and incubation was allowed to proceed for 4 hours in a shaking waterbath at 37° C. This was followed by incubation for 19 hours at 37° C. in an enzyme cocktail to degrade the nuclear material now exposed by lysing the cell organelles. This cocktail contained DNAse I (47 Kunitz U/ml) and RNAse A (1 Kunitz U/ml) in a solution containing magnesium chloride (1 µg/ml) and calcium chloride (3 µg/ml) and buffered using Tris[hydroxymethyl]aminomethane hydrochloride (50 µg/ml) at pH 7.6. (The DNAse I and RNAse A were obtained from Sigma Chemical Company (D-5025 and R-5000) and both were used at a concentration of 17 µg/ml.) Subsequently, the tissue was placed in a 3.5 mM solution of Triton X-100 detergent in sterile water to remove cell debris. This incubation was carried out for 24 hours at 37° C. in a shaking waterbath. The detergent solution was then washed out of the tissue by four washes in sterile water at 37° C. for 30 minutes each. After these washes, the resulting matrix was packaged, cryopreserved, sterilized and placed in storage prior to use as a vascular graft.

For preservation, the tissue was packaged in sterile packages containing Dulbeccos' Modified Eagles Medium solution (DMEM) and 10% dimethyl sulfoxide (DMSO) with 10% fetal bovine serum. Cryopreservation was performed using a controlled rate freezer to reduce the package temperature to −80° C. at 0.5° C. per minute. When the tissue temperature had reached −80° C. each package was removed and placed in liquid nitrogen at −196° C. for long term storage. Sterilization of tissue was performed in the frozen state using a 25–30 kGy dose of gamma radiation. Following sterilization, the tissue was stored at −196° C. in liquid nitrogen until use.

Prior to implantation, the tissue matrix was thawed to remove the cryoprotectant solution from the tissue. The grafts were thawed rapidly to 4° C. in a waterbath at a temperature of 37–42° C. Tissue was quickly transferred to DMEM containing 0.5% mannitol. Mannitol and residual cryoprotectants were removed by dilution with 0.5, 0.25 and 0.0M solutions of mannitol in DMEM. Following these washes, implantation of acellular bovine conduit (that is, the resulting tubular tissue matrix) was performed as an end-to-side interpositional graft in the left and right carotid and left femoral arteries of an adult mongrel dog. The graft lengths were between 9 and 12 cm and the internal diameter of the grafts was between 5 and 10 mm. Implantation was made using standard surgical techniques for vascular graft implantation in these positions. An oral anticoagulant regimen of 325 mg Aspirin and 75 mg Persantin was administered daily to the animal beginning two days prior to the surgical procedure.

At two weeks and at four weeks after surgery, arteriograms were performed to determine the patency of the implanted grafts. The animal was sacrificed and the grafts explanted immediately following the second arteriogram at four weeks after the surgery. Explanted grafts were evaluated for patency and gross appearance and further examined histologically to determine graft microscopic integrity.

Results

During the four weeks duration of the study, the animal behaved normally and there were no complications following surgery. At two weeks and at four weeks after surgery, all three bovine ureter grafts were determined to be fully patent on angiographic examination. At four weeks after surgery, gross analysis of the explanted graft tissue indicated there to have been a healing response that had stabilized the grafts into the surgical site and the patency of all the grafts was confirmed by observing flow through the graft prior to placing the grafts in formalin for fixation. After fixation each graft was cut into seven separate samples for histological analysis. Samples were taken from the native artery at both proximal and distal ends away from the graft. Sections of the proximal and distal anastamosis sites were taken along with the proximal, middle and distal portion of each graft. Following processing, paraffin embedding and sectioning, graft samples were stained using a standard hematoxylin and eosin stain. Microscopic analysis revealed the grafts to be structurally intact. The matrix of the bovine ureter had begun to become re-vitalized through the movement of cellular components from the outer edges of the surgical area. Through this remodeling the grafts were taking on the appearance of natural arterial blood carrying conduits.

EXAMPLE 2

Implantation of Decellularized Porcine Ureter as a Peripheral Vascular Graft in the Dog Methods Porcine ureter tissue was collected and prepared and preserved exactly as described in Example 1 with the exception that the dimensions of tissues selected for processing were 3 mm in internal diameter and 25 cm in length. Implantation of treated porcine ureters was made in an adult mongrel dog as an end-to-end interpositional vascular graft in the left and right femoral arteries and in the left and right carotid arteries. All grafts were examined by arteriogram two weeks after surgery. The animal was sacrificed four weeks after surgery and the grafts were explanted for gross examination and histological evaluation of performance. Histology samples were taken and stained as described in Example 1.

Results

Arteriograms performed two weeks after implantation showed the grafts to be patent. On explantation, gross examination indicated the grafts to be fully patent and difficult to distinguish from the native blood vessel. Histological examination showed the grafts to have become partly recellularized with spindle-shaped cells. This recellularization likely represents the first stages of remodeling into a fully-functional blood-carrying conduit that would be indiscernible from native tissue.

EXAMPLE 3

Implantation of Decellularized Bovine Uterine Artery as a Peripheral Vascular Graft in the Dog Methods Bovine uterine artery tissue was collected and prepared and preserved exactly as described in Example 1. Implantation of treated bovine uterine artery was made in an adult mongrel dog as an end to side interpositional graft in the carotid artery. After 4 weeks of implantation, the grafts were explanted and taken for histological analysis.

Results

At four weeks after implantation, the grafts were patent. Histology indicated these grafts to have begun to take on cells from the host animal.

EXAMPLE 4

Implantation of Decellularized Bovine Gastric Artery as a Peripheral Vascular Graft in the Dog Methods Bovine gastric artery tissue was collected and prepared and preserved exactly as described in Example 1. Implantation of treated bovine uterine artery was made in an adult mongrel dog as an end to side interpositional graft in the carotid artery. After 4 weeks of implantation, the grafts were explanted and taken for histological analysis.

Results

At four weeks after implantation, the grafts were patent. Histology indicated these grafts to have begun to take on cells from the host animal.

EXAMPLE 5

Determination of Burst Strength Characteristics of Decellularized Bovine Ureter

Methods

Three segments of bovine ureter tissue were collected and prepared and preserved exactly as described in Example 1. Using compressed nitrogen gas, the pressure required to burst the graft was determined by slowly increasing the head-pressure of nitrogen applied to the graft. The gas was contained within the graft using standard high-pressure pipe fittings and cable ties. Each graft segment was tested in duplicate and average burst strength for each graft was calculated.

Results

The three grafts were found to burst at 3361, 2456 and 2327 mm Hg, the average being 2715 mm Hg. This magnitude represents a burst strength of around 1.5 times that of the human fresh saphenous vein which is commonly used in bypass surgical procedures.

EXAMPLE 6

Determination of Burst Strength Characteristics of Decellularized Porcine Ureter Methods Six segments of porcine ureter tissue were collected and prepared and preserved exactly as described in Example 2.

Using compressed nitrogen gas, the pressure required to burst the graft was determined by slowly increasing the head-pressure of nitrogen applied to the graft. The gas was contained within the graft using standard high-pressure pipe fittings and cable ties. Each graft segment was tested in duplicate and the average burst strength for each graft was determined.

Results

The six grafts were found to burst at 2068, 5171, 6722, 6722, 5688 and 3620 mm Hg, the average being 4999 mm Hg. This value represents a burst strength of almost 3 times that of human fresh saphenous vein which is commonly used in bypass surgical procedures.

EXAMPLE 7

In Vitro Recellularization of Decellularized Bovine Ureter with Vascular Conduit Cells Methods Three segments of bovine ureter tissue were collected and prepared and preserved exactly as described in Example 1. Each piece of tissue was placed into a 75 cc tissue culture flask containing DMEM and supplemented with 10% fetal bovine serum. Each graft was seeded with endothelial cells or smooth muscle cells to enable cell growth into the graft segments. Cultures were fed using fresh serum-supplemented DMEM two times each week for 4 weeks. After 4 weeks, the tissues were extracted from the culture system and examined using histological sectioning of the tissue and H&E staining.

Results

After four weeks of cell culture, endothelial cells were observed growing on the surface of graft tissue but not internally. In addition, smooth muscle cells were found growing on the surface of the grafts and in the wall of the graft material once they could gain access on the surface of the graft.

EXAMPLE 8

Tissue Graft Derived from Ureter as Aortic Graft in the Dog

Methods

Bovine ureters were used to provide the conduit matrix for the vascular tissue graft. These tissues are available in lengths and diameters suitable for a number of vascular applications and they do not contain valves in the lumen or possess tributaries that require ligation. Ureters were obtained from U.S Department of Agriculture approved slaughterhouses. The tissues were washed in physiological salt solution and transported for tissue preparation on ice within 24 hours of harvest. Ureters were first dissected free of adherent connective tissue and fat and only segments with a 6 mm internal diameter were taken for further processing.

Initial processing consisted of bioburden reduction using a solution of multiple antibiotics as described in Example 1. Removal of greater than 95% of all cellular material was achieved in several steps. First, incubation in sterile water produced hypotonic cell lysis. The resulting tissue matrix was then equilibrated in buffer (PBS) and treated with a solution containing ribonuclease and deoxyribonuclease (see Example 1). An isotonic washout over several days completed the cellular protein removal. Removal of cellular debris was monitored using hematoxylin and eosin staining of histological sections. Tissue matrices were then sterilized by gamma irradiation (25 kGy to 40 kGy) prior to use and analysis of sterility was carried out on each processing batch.

Eight mongrel dogs weighing 50 to 60 lb were anesthetized with sodium thiopental, endotracheally intubated and placed on inhaled isoflurane. The abdomens were prepared and draped in sterile fashion. A midline incision was made and the abdominal aorta distal to the renal arteries was isolated in each dog. Vascular conduits were prepared by washing the tissue matrix in 100 ml of sterile HEPES-buffered Dulbecco's Modified Eagle Medium and a segment approximately 6 cm in length and 6 mm in internal diameter was inserted as an aortic interposition graft using interrupted prolene sutures to construct proximal and distal, end to end, anastomoses. All animals received 325 mg aspirin and 75 mg dipyridamole p.o. daily for 2 days prior to, and for 14 days following, surgery.

Patency and structural stability were observed with angiographic examination following surgery every 6 weeks in the longer survivors and once immediately prior to euthanasia. Two animals were sacrificed at 3 weeks, 3 at 6 weeks, and 1 animal at 13 weeks after surgery. The 2 remaining animals were last evaluated at 43 weeks and are still living. After sacrifice, grafts were removed in bloc incorporating proximal and distal anastamoses inspected grossly and processed for histological analysis.

Following harvest, grafts were fixed in 10% buffered formaldehyde solution. The whole of the graft along with anastamotic sites and proximal and distal native aorta was divided into 7 tissue segments and placed in paraffin blocks for processing. Hematoxylin and eosin-stained sections of these tissues were examined and immunohistochemical analysis was carried out using specific antibiotics to identify the presence of smooth muscle α-actin (α-SMA), desmin and vimentin contractile filaments.

Results

After processing, vascular tissue grafts prepared from bovine ureter showed removal of greater than 95% of bovine cellular material. The remainder consisted of cellular debris and not intact cells. Conduit graft sterility and pyrogen levels of below 20 endotoxin units were demonstrated. Implantation of these interposition grafts into the canine infrarenal aorta was uncomplicated and handling properties of the grafts were similar to normal vascular tissue.

Arteriograms performed on each of the dogs indicated grafts to be fully functional over the 43-week implant period without the appearance of dilation or stenosis. Gross evaluation of all explanted grafts after 3, 6 and 13-weeks of implantation confirmed fully patent grafts. Histologic examination showed a healing response around the graft adventitia with recellularization of the media. A layer of cells on the lumenal surface resembled endothelium. All cells found in the graft were presumed to have originated from the host because the original graft material was acellular. The extent of medial recellularization was approximately 20% at 3-weeks, 30% at 6-weeks and 50% at 13-weeks. Revitalization of the graft media appeared to occur from the adventitial area towards the lumen and as recellularization progressed, there was circumferential organization of cells growing perpendicular to the flow of blood in the conduit.

Analysis of anastomotic sites showed intimal hyperplasia to be minimal and cellular overgrowth was evident at the suture-line creating a smooth transition from native aorta to graft. Histologically, there was no evidence of hyperplastic reaction narrowing the lumen in the graft explanted after 13-weeks. Also, narrowing was not observed angiographically up to 43-weeks after implantation.

Immunohistochemistry staining was used to identify the type of cells present in the recellularized grafts. The proportion of cells expressing smooth muscle contractile proteins were demonstrated using stains containing antibodies to α-SMA, desmin and vimentin. A very large percentage of medial cells at 3, 6 and 13 weeks, were α-SMA positive. Vimentin was also commonly expressed by α-SMA positive cells. Desmin positive cells were less abundant but present in a sub-population. Most of the cells present in the grafts stained positive for at least one of these contractile proteins. As no intact cells were present in the graft conduits prior to implant, all cell-specific immunostaining demonstable for α-SMA, desmin and vimentin was present on cells that had originated from the host.

EXAMPLE 9

Use of Tissue Graft Derived from Ureter as an Arterio-venous Fistula in the Dog Methods Nine segments of treated bovine ureter tissue graft conduit, prepared as described in Example 9, (20 cm×6 mm ID) were implanted as arteriovenous grafts in the carotid artery (CA) and jugular vein (JV) (n=5), or in the femoral artery (FA) and femoral vein (FV) (n=4) in 6 adult dogs. A control group of 7 dogs received 11 (6 mm ID) polytetrafluoroethylene (PTFE) grafts (7 in the CA and JV, and 4 in the FA and FV). All grafts were matured for 14 days and then sham-accessed once weekly with two 17-gauge hemodialysis needles. Routinely over a 6-month period, patency was assessed and blood was drawn to monitor CBC and clotting factors. Histological analysis was performed in a sub-group of explanted grafts at 2, 4, 10 and 24 weeks.

Results

27% (3/11) of the PTFE grafts became infected, while none of the tissue graft conduits prepared in accordance with the present invention became infected during the study. The patency rate of the tissue graft conduit was 86% compared to 72% for the PTFE grafts. The white blood cell count was not elevated in either group at 2 and 7 weeks and blood clotting factors were also unchanged. The hemostasis times after sham sticking of the grafts was longer (mean 10 minutes) in the PTFE grafts compared to the tissue graft conduits (mean 3 minutes). Histology at 10-weeks showed tissue graft conduits to have undergone recellularization of the tunica media with host spindle shaped cells as well as excellent incorporation into surrounding tissues as evidenced by capillary ingrowth into the tunica adventitia. PTFE grafts showed no significant cellular ingrowth and an absence of luminal endothelium.

EXAMPLE 10

Packaging and Sterilization of Tissue Graft

Packaging

Tissue product is packaged in heat sealed clear polyester pouches containing phosphate buffered saline and stored at 40 centegrade for up to 7 days prior to sterilization.

Shipping

Three frozen 2 lb cold gel bricks are placed in the bottom of a pre-chilled 19"×14.5"×22" cardboard container insulated with 2" polyurethane foam. Two cardboard separators are placed on top of these.

Three cold 2 lb gel bricks are added followed by product load (1,100 cubic inches).

Two filler bags are used as temperature indicators on which various temperature indicator strips are present, the filler bags are placed among the samples. A seven-day mechanical temperature recorder is also placed among the samples.

Three cold 2 lb gel bricks are place on top of the product load followed by a cardboard separator and three frozen 2 lb gel bricks. A foam plug is placed on top of the last layer of bricks and the box is closed.

The box is shipped to sterilization facility for sterilization by gamma irradiation at 25–40 kGy. The box is then returned and product is unpacked and stored at room temperature until use. The total tissue time between packing and unpacking is advantageously less than 100 hours and the temperature is maintained throughout this period at 2° C.–8° C.

Storage

The tissue graft can be stored at room temperature for 2 years.

All documents cited above are hereby incorporated in their entirety by reference.

One skilled in the art will appreciate from a reading of this disclosure that various changes in form and detail can be made without departing from the true scope of the invention.

What is claimed is:

1. A tissue graft produced by a method consisting essentially of the steps of:
   i) washing a starting tissue obtained from a human or animal ureter with a bioburden reducing agent so that said starting tissue is disinfected,
   ii) decellularizing the disinfected tissue resulting from step (i) with water or an aqueous hypotonic buffer that lyses cells of said disinfected tissue so that a tissue matrix is formed, and
   iii) contacting said tissue matrix resulting from step (ii) with a nuclease so that nucleic acid associated with said tissue matrix is degraded, and
   iv) washing said tissue matrix resulting from (iii) so that cellular or extracellular debris is removed and said tissue graft is produced.

2. The tissue graft according to claim 1 wherein, after step (iv), said tissue matrix is sterilized.

3. The tissue graft according to claim 1 wherein said tissue graft is cryopreserved.

4. The tissue graft according to claim 1 wherein said starting tissue is obtained from a bovine or porcine ureter.

* * * * *